(12) United States Patent
Heinrich (10) Patent No.: US 10,421,069 B2
(45) Date of Patent: Sep. 24, 2019

(54) MULTIFUNCTIONAL SYSTEM FOR PARTICLE SEPARATION

(71) Applicant: Hans-Werner Heinrich, Spring Valley, CA (US)

(72) Inventor: Hans-Werner Heinrich, Spring Valley, CA (US)

(*) Notice: Subject to any disclaimer, the term of this patent is extended or adjusted under 35 U.S.C. 154(b) by 693 days.

(21) Appl. No.: 14/792,397

(22) Filed: Jul. 6, 2015

(65) Prior Publication Data
US 2015/0343351 A1 Dec. 3, 2015

(51) Int. Cl.
*B01L 3/00* (2006.01)
*G01N 1/40* (2006.01)

(52) U.S. Cl.
CPC ......... *B01L 3/502* (2013.01); *B01L 2200/023* (2013.01); *B01L 2300/042* (2013.01); *B01L 2300/0681* (2013.01); *G01N 2001/4088* (2013.01)

(58) Field of Classification Search
CPC ............. B01L 3/502; B01L 2300/0681; B01L 2200/023; B01L 2300/042; G01N 2001/4088
See application file for complete search history.

(56) References Cited

U.S. PATENT DOCUMENTS

| | | | | |
|---|---|---|---|---|
| 3,300,051 A | * | 1/1967 | Mitchell | B01L 3/5021 210/339 |
| 2004/0005246 A1 | * | 1/2004 | Efthimiadis | A61B 10/0051 422/534 |
| 2015/0290640 A1 | * | 10/2015 | Goettke | A61B 5/150351 220/288 |
| 2015/0328634 A1 | * | 11/2015 | Fonseca | B01L 3/5088 435/6.12 |

* cited by examiner

*Primary Examiner* — Krishnan S Menon
*Assistant Examiner* — Waqaas Ali
(74) *Attorney, Agent, or Firm* — S&L US IP Attorneys, P.C.; Timothy Marc Shropshire (57) ABSTRACT

A multifunctional system for particle separation and/or treatment for the usage in biological and medical research, to detect and to treat diseases with a modular system consisting out of the filter/strainer device and the auxiliary devices lower connector with tube adaptor and upper screw cap connector. All parts of the modular system can be airtight connected and by means of a valve used with higher pressure, lower pressure or without pressure equalization.

20 Claims, 7 Drawing Sheets

MULTIFUNCTIONAL SYSTEM FOR PARTICLE SEPARATION

FIELD OF THE INVENTION

This invention relates to a filter apparatus for removing or separating particles above or below a certain diameter from a suspension/dispersion of different biological origin using the filter system with laboratory vessels or connecting it to a flexible tubing system.

BACKGROUND

Separation of matter is one of the oldest methods in experimental research. Many solutions were made to fit the devices to the different sizes of vessels and variations of the openings (U.S. Pat. No. 2,703,670A, CH 241194A, U.S. Pat. No. 2,331,234A, WO 2009096790A1, US 20130306576A1).

All solutions have the same characteristic, they are loosely placed on the opening of the container, which allows the pressure exchange between the separation device and the laboratory container thereby facilitating the free flow of the liquid. The varying diameters of the vessels is typically bridged by giving the outflow a conical shape (funnel shape).

WO 2009096790 A1, where the filter is provided with a plurality of supporting edges which fit to the outside of a vessel. The filter rests via the supporting edges on the vessel. Filters of this kind which simply sit on top of a vessel (tube) tend to tilt over.

The separation of particles and molecules by means of filtration is an increasingly more important tool in experimental research and has led during the last decades to new and revolutionizing applications like sterile filtration of media, dialysis or desalination of salt water.

With the use of particles as the carrier of molecule specific binding moiety, filters with greater mesh size are needed. Therefore, a 20 μm mesh is commonly used in medical devices for immune aphaeresis. But also in biological/medical research have filters with mesh sizes in μm range found a wide usage for separation purposes.

WO2012066503 reveals a container for selective transfer of specimens of biological material by using a separation system hanging a centrifugation. EP0237674A2 also describes a filter which hangs inside the centrifuge basket.

WO 1993001271 describes a filter hanging inside a vessel leaving no space between the side walls of the filter and the container, which impairs the exchange of pressure when the filter is filled with fluid. This can impair with the free flow, especially if the specimen is of viscous consistence. Then the filters have to be lifted up manually to allow the air exchange.

The volume of the filter systems described above the sieve, is limited and mostly even is too small to hold the sample volume of a standard tube. A constant refill is necessary during filtration.

But the small size of the filter/mesh area in devices for laboratory use is the result of the practical laboratorial work. Only a limited amount of sample material is needed, all necessary other buffers and disposables are minimized, rack space is reduced, more samples can be handled parallel, and, at the end, costs are reduced.

EP2664367A1 describes a cell strainer which is compatible with tubes of different opening sizes, i.e. fits on at least both the standard 15 ml and 50 ml laboratory tubes. The strainer consists of two parts, an "upper portion" which is the original strainer, and a "lower portion" which is an adaptor between the strainer and the standard tubes.

The lower adaptor portion has shoulders or flanges which define at least one recess for air exchange. It is designed to fit into the openings of different sizes by having shoulders or projections which have the diameter of the opening of a first tube, and a second section having an inner and outer wall as a holder for the neck of a second tube. The cell strainer according EP2664367A1 can be used for the removal of cell aggregates or large particles after tissue dissociation or from blood samples of up to 50 ml to obtain uniform single-cell suspensions. The design of the filters allows improved ventilation during filtration, and so avoids clogging of the filter. But the upper parts (the strainer) cannot be used separately from the lower (adapter) part. They cannot be inserted in centrifuge tubes. They cannot be flipped around on a standard tube to backwash the filter surface. They cannot be connected to a vessel which contains samples.

There is a need for a versatile filter apparatus which provides sufficient filter efficiency but is also compatible with small tube sizes; filters which can also be used inside a centrifuge tube, filters which can be used in both flow directions and can be connected to a sample reservoir, and, last but not least, provide a reaction room to work on/with the separated particles.

SUMMARY OF THE INVENTION

A goal of the invention is to provide a modular apparatus of filters or strainers which
  Can be used in a free flow system but also under lower or higher pressure or without pressure exchange between filter and outlet
  Create a reaction room to pursue experiments with/on the separated particles
  Can be closed with a cap
  Can be used hanging inside of a tube or sitting on top of a tube
  Can be used for the common tube sizes of 50 ml, 15 ml, 2 ml, but also larger than the 50 ml tubes
  Can be used in both flow directions to flash back the separated particles or their experimental outcome
  Can be permanently or temporarily connected to vessels which contain the specimen of separation
  Fits standard tissue culture plates to submerse the filter surface with buffer for further treatment of separated particles This goal is accomplished with a modular apparatus consisting out of the filter apparatus and the auxiliary devices Lower Connector with a tube adaptor and an Upper Connector which also can be used as a cap.

All parts of the modular system can be airtight connected and by means of a valve used with higher pressure, lower pressure or without pressure equalization.

The Filter/Strainer 1 fits airtight in the Lower Connector 2. The filter membrane/mesh is situated at a distance to the lower ending of the device which allows submersion of the mesh when it is used in commercial tissue culture plates. The connection between the filter/mesh and the housing is preferably curved to reduce adhesion effects of liquids on this area. The upper part of the device has an outer screw thread which can be used for different upper connectors 15. The outer diameter of the filter housing is smaller as is the inner diameter of commonly used laboratory tubes, preferably 50 ml tubes.

A protrusion close to the upper end of the filter housing allows the positioning of the filter device on top of the commonly used laboratory tubes hanging inside.

The filter housing has a conical shape to stack several filters together.

The part above the protrusion which carries the outer screw thread fits commonly used laboratory tubes and allows flipping the filter housing around working now in counter flow direction.

Protrusions of different highs vertical on the protrusion gives the flipped over filter a slanted position on the laboratory tube to optimize a back flush.

The lower connector 2 and the tube adaptors 3, 20 are two separate parts. The connector 2 fits air-tight commonly used laboratory tubes, preferably 50 ml tubes. The upper opening holds air-tight the filter/strainer housing in a way that the filter housing does not stick out within the connector 2. An opening though the filter holding part of the adaptor 2 can be used as a valve and allows pressure equilibration for free flow of samples but can also be closed or use to create a higher or lower pressure inside the tube-filter-system by different means, e.g. a common syringe. The opening has to be localized under the filter/mesh.

No flow of liquid trough the strainer is possible when the valve is closed. The part on top of the filter/mesh becomes a reaction compartment to treat samples.

The inner shape of the adaptor C has funnel geometry when the tube-filter-system is turned around of 180°.

The tube adaptor C is basically of a narrowed tube of at least two diameters created connected by at least one neck. The tube part with the largest diameter fits air-tight in the inner part of the connector B. It creates now at least one tube which can be air-tight inserted in the commonly used laboratory tubes of e.g. 15 ml or 2 ml. The same principle can be used for connecting a flexible tube. Multiple diameters for two different tube sizes are demonstrated in Fig . . . .

The upper Connector D in its simplest form can function as a screw cap which closes air-tight the filter/strainer housing. The crew cap can integrate a handle to avoid tilting over or slipping of the filter/strainer. It can have an opening to connect it with a syringe or a flexible tube. Another example is the opening with connects the filter/strainer housing with a commonly used sample tubes via a screw connection.

The multifunctional filter apparatus according the invention can be assembled according the needs of the experiments as an open or closed system fitting different sizes of typical laboratory vessels. It can be used for the purpose of separating particles e.g. somatic cells and cell agglomerates, cellular components, synthetic particles alone or loaded with target compounds.

The system can be used without and with centrifugation.

The air-tight connection with the laboratory tube, the special internal shape of the connector and the equipment with a valve for pressure regulation below the filter membrane/mesh creates a reaction compartment on top of the membrane which can be used to treat the isolated/separated particles e.g. for nucleic acid or protein isolation.

The multifunctional filter apparatus according the invention can be used in flow and counter-flow direction. In the simplest way to flash back the separated particle in a laboratory tube for further treatment. The tube under the filter apparatus can contain certain liquids which by rotating of the filter-tube-system by 180° now flow through the isolated/separated particles for further treatment. The same effect will be achieved by pumping the liquid in the upper part of the filter apparatus by e.g. a syringe.

The multifunctional filter apparatus according the invention can be used to transfer separated cells (e.g. circulating cancer cells from blood samples, blood stem cells, or other cells derived from tissue samples) in commonly used tissue culture plate. The strainer fits in the cavities of common cell tissue plates. The separating mesh will be submersed by the medium. The isolated target cells e.g. being attached to a solid carrier can be detached and the target cells will fall down through the mesh and attach/grow on the tissue plate.

The multifunctional filter apparatus according the invention can be air-tight closed with a screw cap. This improves product and/or people protection. The screw cap can be modified with an adaptor for a syringe or a flexible tube. An unlimited amount of sample or buffer can now be pumped through the filter/strainer system in direct flow but also against the gravity (180° rotated)

The multifunctional filter apparatus according the invention can be used in combination with commonly used sample tubes by a screw cap adaptor to the sample tube. The sample tube can carry a mixture of anti-coagulant and solid carriers (e.g. functionalized beads).

After mounting the sample tube to the filter/strainer system, the solid carrier-target complex can be isolated and further treated.

The multifunctional filter apparatus according the invention can be used in combination with a second filter/strainer which hangs inside the first. The filter/strainer can have different mesh sizes.

BRIEF DESCRIPTION OF THE PICTURES

DETAILED DESCRIPTION

Figure 1:
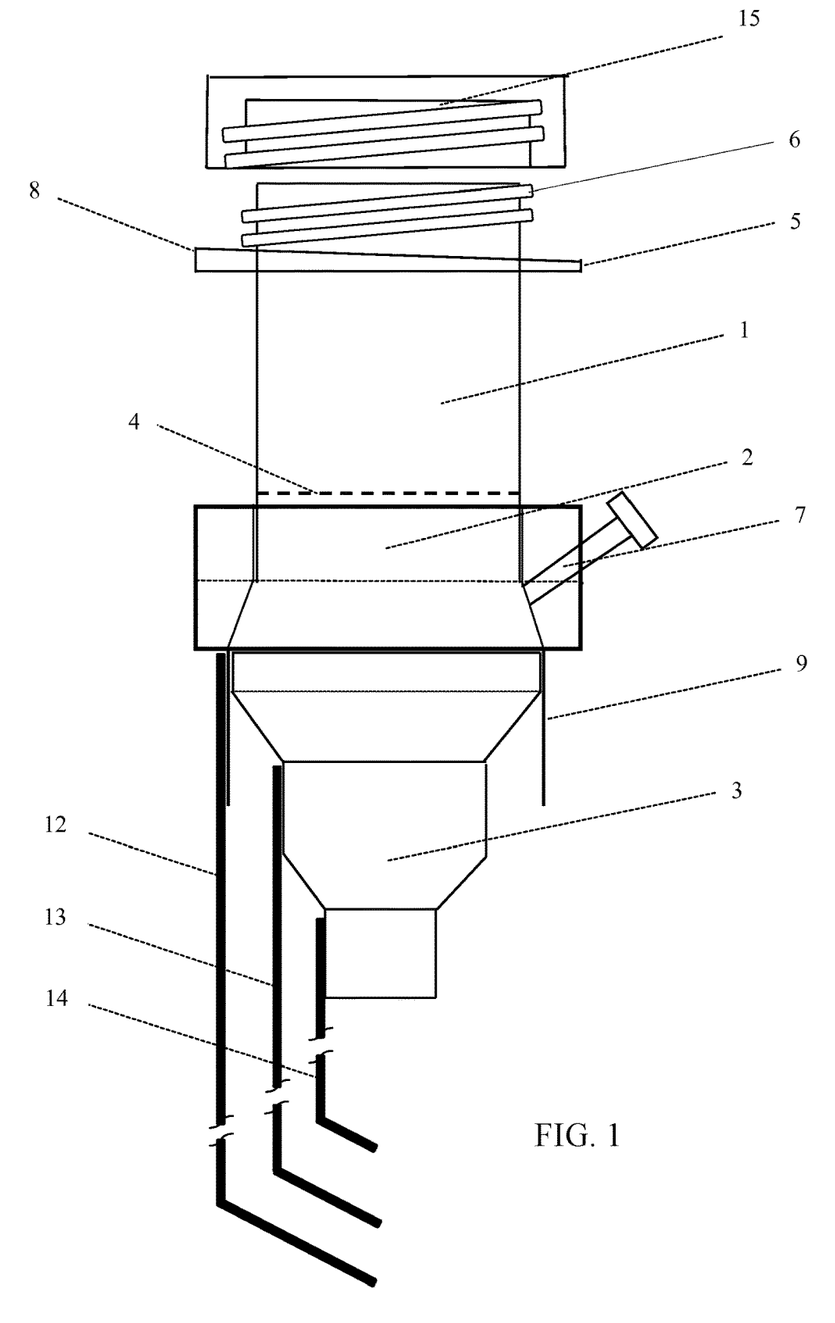
FIG. 1 shows a schematic side view of the strainer-adaptor-complex

FIG. 1 shows a schematic side view of the multifunctional filter apparatus according to the invention. The strainer 1 is air-tight inserted in the connector 2. The connector 2 ends in the lower part in a tube like lengthening (9) which fits air-tight in a common laboratory tube, preferable a 50 ml tubes (12). A closable opening 7 inside the connector can be used to regulate the pressure within the strainer system. The separate tube adaptors 3 and 20 (FIG. 2) can be air-tight inserted inside the connector to allow the usage of different sizes of laboratory tubes, preferably 15 ml (13) or 2 ml (14) but also larger ones. The rim 5/8 close to the upper end of the filter/strainer 1 overhangs the filter/strainer body and can sits on the e.g. 50 ml laboratory tube. The out site screw thread 6 is used to close the upper part of the filter apparatus by means of a crew cap 15. The screw threat is recessed to the rim 5 (FIG. 3). The diameter c) of the screw thread upper part is smaller than the opening b) of e.g. a 50 ml laboratory tube. The diameter a) of the rim 5/8 is at least the same as the outer diameter of the tube 12.

Figure 4:
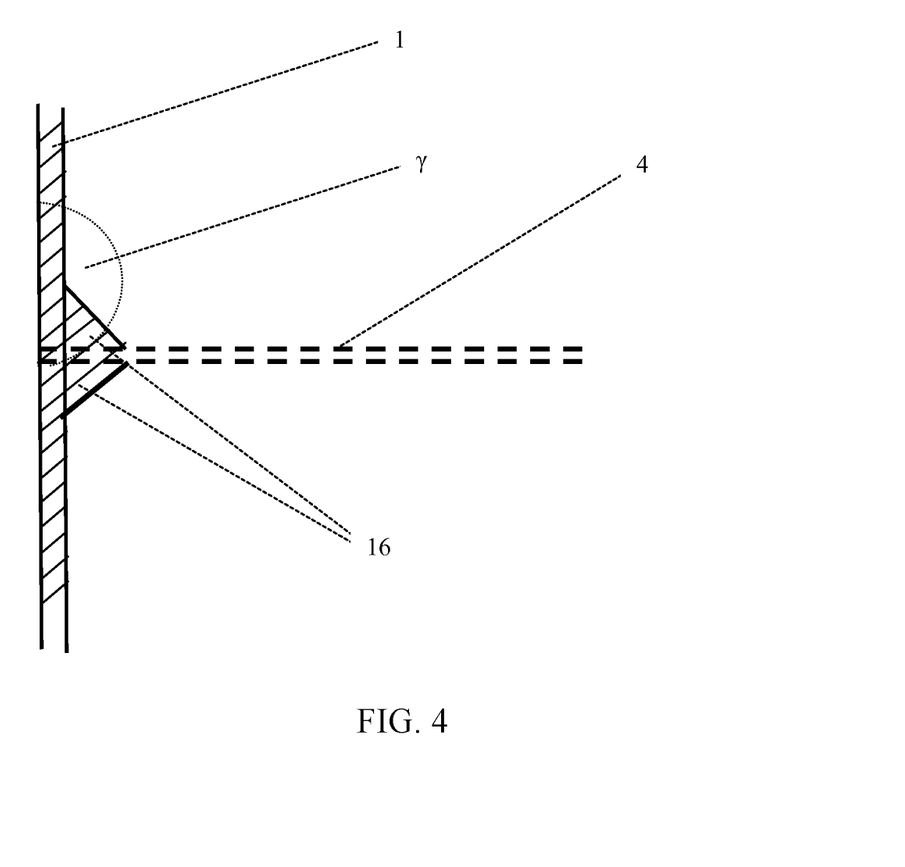
FIG. 4 shows a schematic side view of the mounting of the membrane/mesh to the strainer body

The filter/mesh 4 is an integrated part of the filter/strainer body (FIG. 4). It is injection-molded. Commonly available strainers use ultrasound to glue the filter/mesh to the strainer body. One embodiment of the invention is the triangle or round molding 16 between the filter housing and the mesh to avoid the 90° corner which is in commonly available strainer/filter the cause for concentration of particles/cells due to the adhesion effect of liquids. In case of forming a triangle, the angle γ between filter 4 and housing 1 is larger than 90°

The mechanical stability of the injection molded mesh makes it suitable for tissue disintegration with or without chemical or enzymatic support.

The filter/strainer system according the invention may have filter areas with a mesh size between 1 and 1,000 μm.

Figure 2:
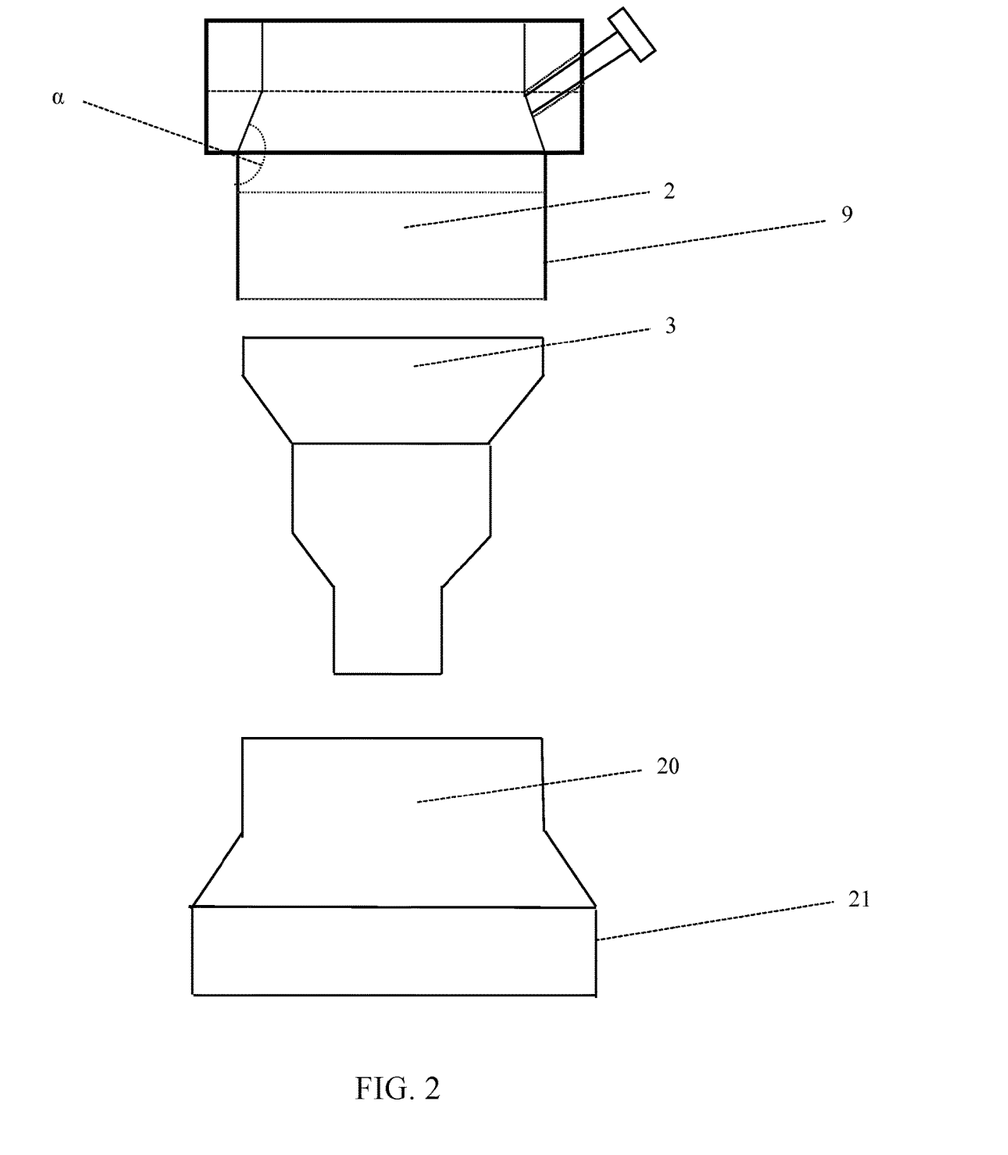
FIG. 2 shows a schematic side view of the connector with the tube adaptors.
Figure 3:
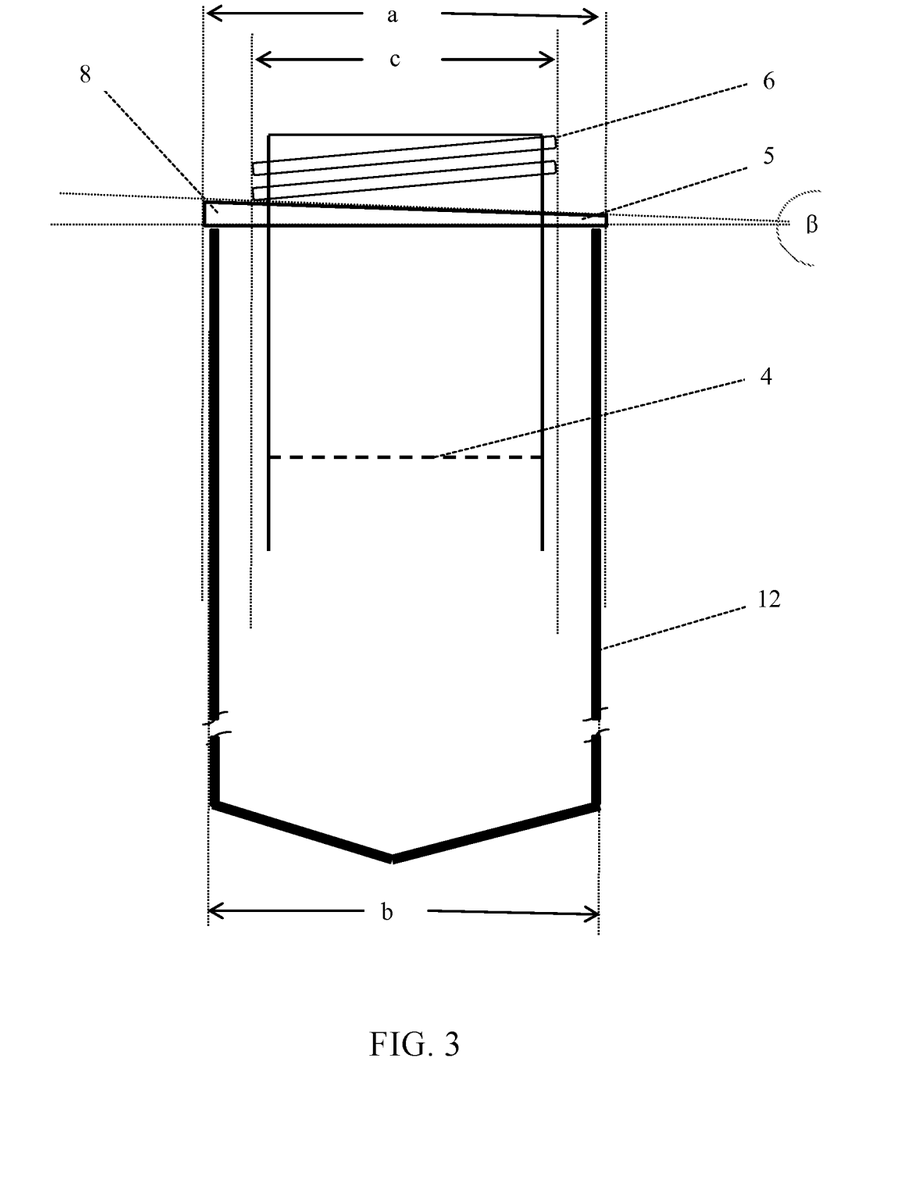
FIG. 3 shows a schematic side view of the strainer

FIG. 2 shows the separation of the filter apparatus for the mostly used 50 ml tubes 2 from the tube adaptors 3, 20 to fit smaller laboratory tubes (3), preferably 15 ml and 2 ml tubes, but also larger ones (20). It gives the user more freedom to operate and alleviates the laboratory work for the majority of applications. The 50 ml and the 2 ml variation are designed to avoid dead space when used 180° turned around. In the 50 ml variation the angle (α) between the tube and the filter/strainer body is smaller than 180° and bigger than 90°.

Tube adaptor to larger laboratory vessels (20) is also part of the embodiment.

Another embodiment (FIG. 3) is that the filter/strainer can be used hanging inside a commonly used laboratory tube, preferably 50 ml which is useful when the centrifugation of the filter/strainer is needed. The filter/strainer according the invention can be flipped around on the top of commonly used laboratory tube. The slanted ring 5/8 holds the 180° rotated filter/strainer on the tube and gives the strainer for this application an inclined filter/mesh, formed by angle β, which improves the collection of back-flashed material. The slanted position can be achieved by one ring 5 (FIG. 5.) or by a series of protrusions 8 (FIG. 3) of different length standing vertical on the ring.

Figure 5:
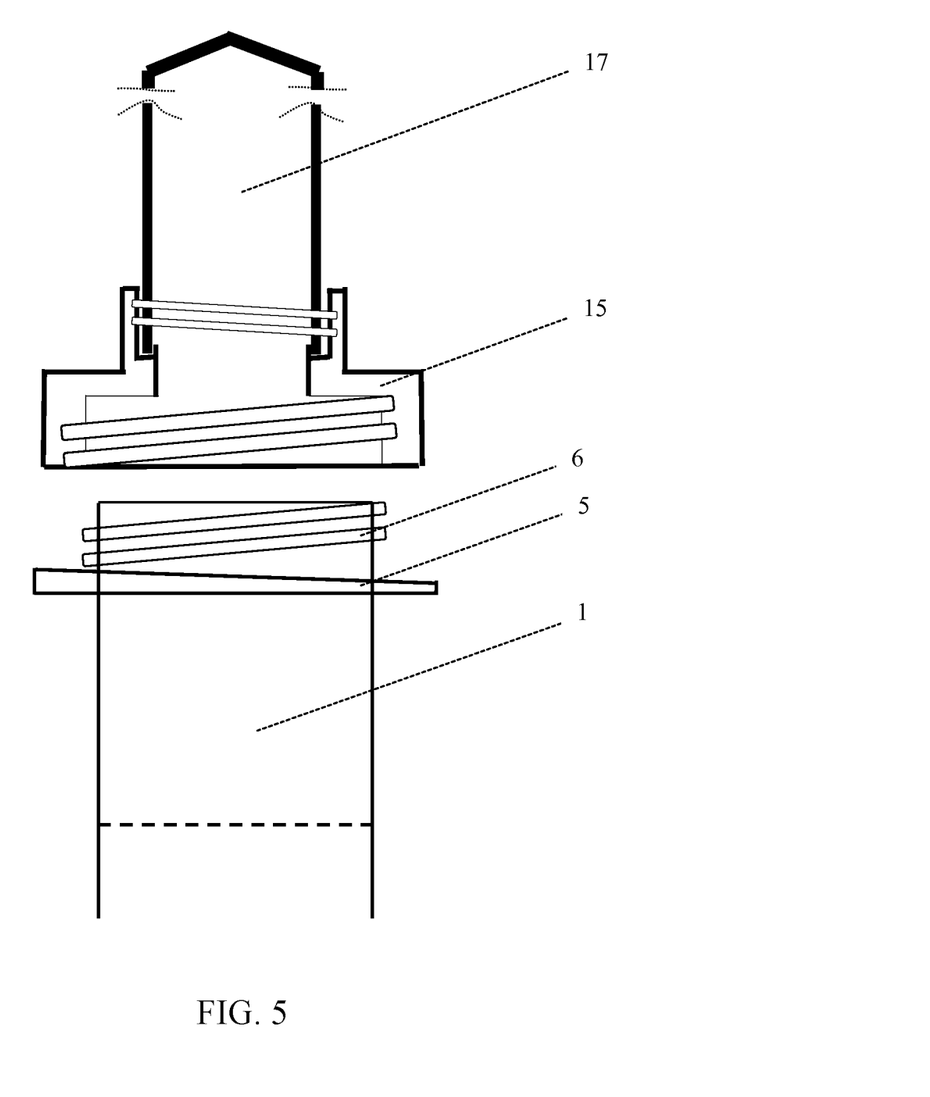
FIG. 5 shows a schematic side view of one version of screw cap adapter to a sample tube

Another embodiment of the filter apparatus according the invention is the creation of a reaction compartment on top of the filter/mesh by inserting the filter/strainer in the connector which is air-tight inserted in a laboratory tube. The opening 7 allows venting of the system needed for the free flow. After the particle separation the opening 7 is closed. The pressure exchange between the tube and the outside is interrupted. That makes the free flow impossible. The separated particles can now be treated with any liquid. The screw cap 15 can be used to add or to remove liquids or reaction products (FIG. 5, 6)

Another embodiment is the screw thread 6 and the screw lid 15 on the upper part of the filter/strainer housing. Commonly used strainers are open, an attachment with other devices is not intended or not provided. The more diverted and complex use for strainers in biological and medical research and diagnostic needs a system to protect the sample and/or the person. This can be achieved by the screw cap 15 according to the invention. This screw cap can be equipped with a handle and closes air-tight the filter/strainer from the top.

The screw cap can facilitate as an adaptor to add further devices, like commonly used sample tubes 17, an adaptor to a flexible tube.

Figure 6:
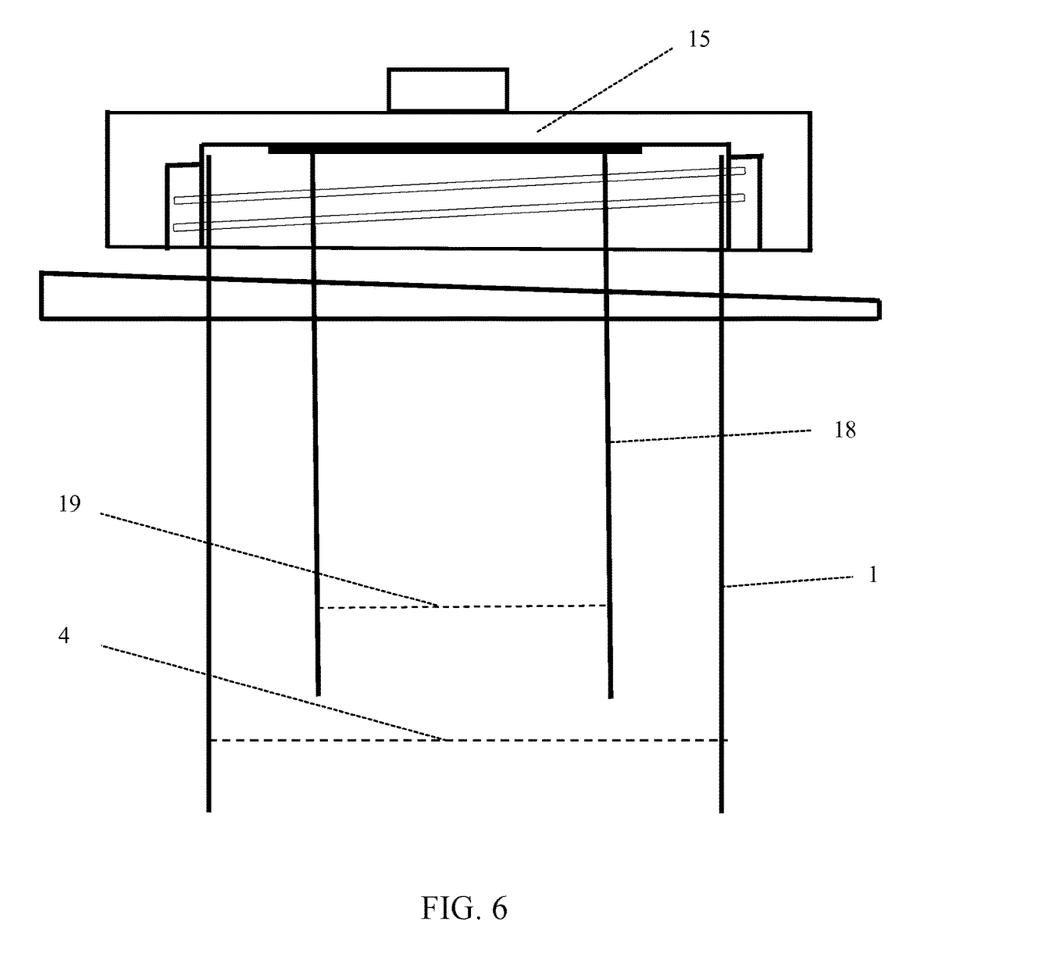
FIG. 6 shows a schematic side view of one version of the crew cap adapter with second strainer hanging inside

Another embodiment of the invention is to use the screw cap adaptor as a holder for devices which can be inserted into the filter/strainer. FIG. 6 shows a second filter/strainer 18 connected to the screw cap adaptor. This second filter/strainer can be part of a specimens collecting system to collect specimens like blood or other body liquids from patients. Functionalized solid carriers like beads of different size can be part of the specimens collecting system or can be added later. At least two different parameters including cells can be isolated by use of two different mesh sizes (4, 19).

Other embodiments are devices to move or to treat the liquid

Figure 7:
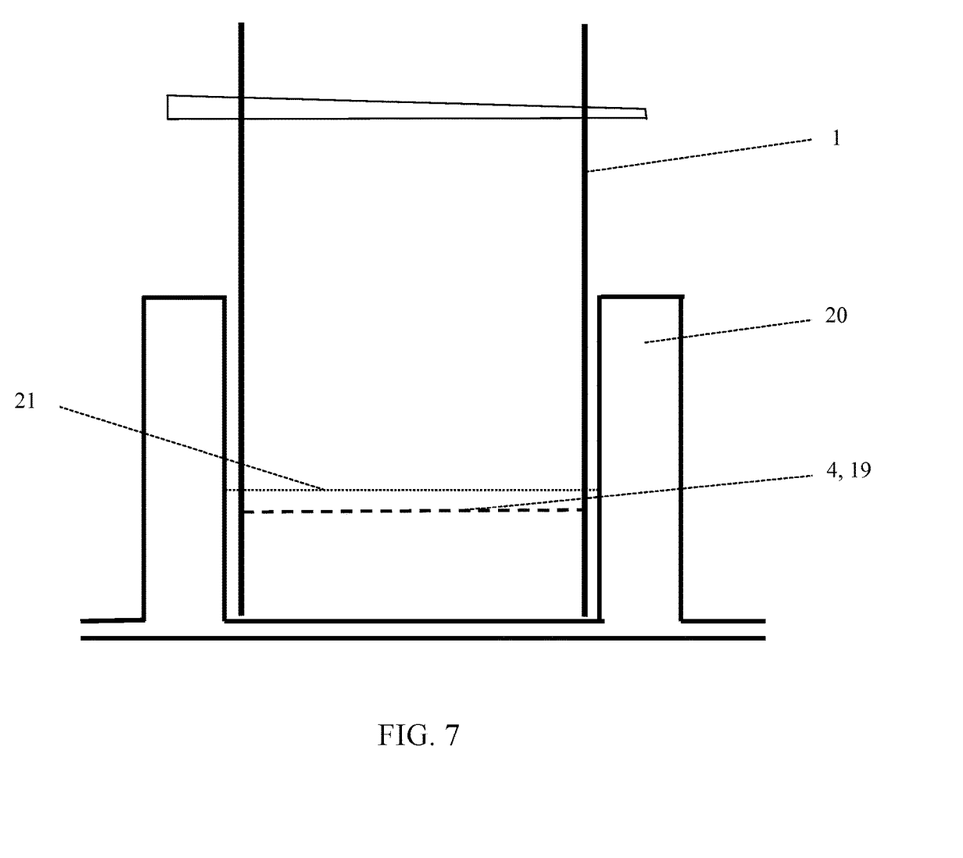
FIG. 7 shows a schematic side view of the strainer being used to transfer cells in a tissue plate cavity

Another embodiment is the use of the strainer as part of a system to separate, isolate and cultivate cells from different origin (FIG. 7). The growing availability of specific antibodies against different types of somatic cells allows targeting specific cells for research, diagnostic and therapy. A certain cell number (cell density) is needed to cultivate primary cells. They liberate "growth factors" which supports attachment and multiplication of cells. In case of not enough cells—not enough "growth factors" were produced with effect that the harvested cells do not growth. The separation of the sufficient amount of target cells is limited by the available sample amount and/or the low number of targets in the specimens. These targets can be specifically caught by functionalized particle. The loaded strainer mesh 4, 19 is submersed by the appropriate medium 21 in the cavity of the tissue plate 20 to detach the cells from the beads.

I claim:

1. A particle separation system comprising:
    a) a tubular body including:
        i) a rim circumferentially engaged to an exterior of an upper portion of the tubular body; and
        ii) a first filter positioned within the tubular body;
    b) a connector that directly engages a lower portion of the tubular body, the connector including a valve that extends through an exterior wall of the connector; and
    c) a tube adaptor that directly engages a lower portion of the connector, the tube adaptor including a stepped architecture, wherein each step has a unique diameter.

2. The system of claim 1, wherein the tubular body further includes threading positioned between the rim and an upper end of the tubular body, wherein the system further comprises a screw cap including a first threaded bore extending into and through a first end of the screw cap, wherein the screw cap threadingly engages the upper portion of the tubular body.

3. The system of claim 2, wherein the screw cap further includes a second threaded bore extending into and through a second, opposing end of the screw cap, wherein the first threaded bore and the second threaded bore are conjoined.

4. The system of claim 3, wherein the screw cap comprises a second filter, wherein a mesh size of the first filter is different than a mesh size of the second filter.

5. The system of claim 1, wherein an upper surface of the rim forms an oblique angle relative to a longitudinal axis of the tubular body.

6. The system of claim 5, wherein a lower surface of the rim is oriented perpendicular to the longitudinal axis, wherein the rim includes a plurality of vertically-disposed protrusions of varying lengths that collectively form the upper surface.

7. The system of claim 5, wherein a largest outer diameter of the upper portion of the tubular body between the rim and an upper end of the tubular body is smaller than an inner diameter of a laboratory tube, wherein a diameter of the rim is at least as large as an outer diameter of the laboratory tube.

8. The system of claim 7, wherein the upper portion of the tubular body includes threading.

9. The system of claim 1, wherein the tubular body further includes a first molding positioned around an inner circumference of the tubular body, wherein the first molding abuts a first side of the first filter.

10. The system of claim 9, wherein the tubular body further includes a second molding positioned around the inner circumference of the tubular body, wherein the second molding abuts a second side of the first filter.

11. The system of claim 10, wherein a cross-section of each of the first molding and the second molding is triangular.

12. The system of claim 10, wherein a cross-section of each of the first molding and the second molding is in the form of a quarter circle.

13. The system of claim 1, wherein an outer diameter of a most distally located step is smaller than an outer diameter of a most proximally located step, wherein each step matingly engages an inner diameter of a corresponding laboratory tube.

14. The system of claim 13, wherein the outer diameter of the most proximally located step matingly engages an inner diameter of a 50 mL laboratory tube, wherein the outer diameter of the most distally located step matingly engages an inner diameter of a 2 mL laboratory tube, and wherein an outer diameter of an intermediate step matingly engages an inner diameter of a 15 mL laboratory tube.

15. The system of claim 13, wherein an outer diameter of the lower portion of the connector is smaller than an outer diameter of an upper portion of the connector, wherein the outer diameter of the lower portion of the connector matingly engages an inner diameter of a laboratory tube.

16. The system of claim 3, wherein a circumference of the first threaded bore is different than a circumference of the second threaded bore.

17. The system of claim 3, wherein a threading of the first threaded bore and a threading of the second threaded bore are non-contiguous with one another.

18. The system of claim 3, wherein the first threaded bore and the second threaded bore are axially aligned with one another.

19. A particle separation system comprising:
a) a housing body including:
  i) a rim circumferentially engaged to an exterior of an upper portion of the housing body; and
  ii) a first filter positioned within the housing body;
b) a connector that directly engages a lower portion of the housing body, the connector including a valve that extends through an exterior wall of the connector; and
c) a tube adaptor that directly engages a lower portion of the connector, the tube adaptor including a stepped architecture, wherein each step has a unique diameter.

20. The system of claim 19, wherein an upper surface of the rim forms an oblique angle relative to a longitudinal axis of the housing body.

* * * * *